United States Patent
Yan (10) Patent No.: US 11,103,549 B2
(45) Date of Patent: Aug. 31, 2021

(54) USE OF HISTONE METHYLTRANSFERASE INHIBITORS AND HISTONE DEACETYLASE INHIBITORS FOR THERAPY OF PHELAN-MCDERMID SYNDROME

(71) Applicant: Asddr, LLC, Getzville, NY (US)

(72) Inventor: Zhen Yan, Getzville, NY (US)

(73) Assignee: ASDDR, LLC, Getzville, NY (US)

( * ) Notice: Subject to any disclaimer, the term of this patent is extended or adjusted under 35 U.S.C. 154(b) by 84 days.

(21) Appl. No.: 16/472,768

(22) PCT Filed: Dec. 20, 2017

(86) PCT No.: PCT/US2017/067581
§ 371 (c)(1),
(2) Date: Jun. 21, 2019

(87) PCT Pub. No.: WO2018/119065
PCT Pub. Date: Jun. 28, 2018

(65) Prior Publication Data
US 2021/0008155 A1    Jan. 14, 2021

Related U.S. Application Data (60) Provisional application No. 62/438,044, filed on Dec. 22, 2016.

(51) Int. Cl.
| A61K 38/00 | (2006.01) |
| A61K 38/15 | (2006.01) |
| A61K 31/517 | (2006.01) |

(52) U.S. Cl.
CPC ............ *A61K 38/15* (2013.01); *A61K 31/517* (2013.01)

(58) Field of Classification Search
CPC .............................. A61K 38/15; A61K 31/517
See application file for complete search history.

(56) References Cited

FOREIGN PATENT DOCUMENTS

| WO | 2012/149472 A2 | 11/2012 |
| WO | 2015/192981 A1 | 12/2015 |
| WO | 2017/201199 A1 | 11/2017 |

OTHER PUBLICATIONS

Oberman et al. Autism spectrum disorder in Phelan-McDermid syndrome: initial characterization and genotype-phenotype correlations. Oberman et al. Orphanet Journal of Rare Diseases (2015) 10:105 (Year: 2015).*
Phelan Mary. Deletion 22q13.3 syndrome. Orphanet Journal of Rare Diseases 2008, 3:14 (Year: 2008).*
Jiang H.Preclinical studies of a novel epigenetic therapy for Prader-Willi syndrome (Year: 2016).*
Foley et al. Class I histone deacetylase inhibition ameliorates social cognition and cell adhesion molecule plasticity deficits in a rodent model of autism spectrum disorder. Neuropharmacology 63 (2012) 750-760. (Year: 2012).*
Foundation for Prader-Willi Research, Preclinical studies of a novel epigenetic therapy for Prader-Willi syndrome, Oct. 8, 2016, 3 pages. <https://web.archive.org/web/20161008193539/https://www.fpwr.org/fpwr-funded-projects/preclinical-studies-of-a-novel-epigenetic-therapy-for-prader-willi-syndrome/>.
Oberman, L.M., et al., Autisum spectrum disorder in Phelan-McDermid syndrome: initial characterization and genotype-phenotype correlations, Orphanet Journal of Rare Disease, Aug. 27, 2015, vol. 10, pp. 1-9.

* cited by examiner

*Primary Examiner* — James H Alstrum-Acevedo
*Assistant Examiner* — Mercy H Sabila
(74) *Attorney, Agent, or Firm* — Hodgson Russ LLP (57) ABSTRACT

Provided are methods for prophylaxis and/or therapy for Phelan-McDermid Syndrome (PMS) and autism spectrum disorder (ASD). The methods involve administering a histone methyltransferase (HMT) inhibitor, a histone deacetylase (HDAC) inhibitor, or a combination thereof, such that one or more symptoms of the PMS and/or the AMD are reduced.

10 Claims, 8 Drawing Sheets

USE OF HISTONE METHYLTRANSFERASE INHIBITORS AND HISTONE DEACETYLASE INHIBITORS FOR THERAPY OF PHELAN-MCDERMID SYNDROME

CROSS REFERENCE TO RELATED APPLICATIONS

This application claims priority to U.S. provisional application No. 62/438,044, filed Dec. 22, 2016, the disclosure of which is incorporated herein by reference.

BACKGROUND OF THE DISCLOSURE

Phelan-McDermid Syndrome (PMS), also called 22q13 Deletion Syndrome, is a genetic condition caused by haploinsufficiency of Shank3 gene (located on 22q13.3, Bonaglia et al., 2001). Using gold-standard diagnostic assessments, it has been found that 84% of PMS patients meet criteria for autism spectrum disorder (ASD), including 75% meeting criteria for autism (Betancur and Buxbaum, 2013). It is estimated that Shank3 deletion or loss-of-function mutations contribute to approximately 1% of all ASD cases and 2% of the ASD cases with moderate to profound intellectual disability (Durand et al., 2007; Moessner et al., 2007; Leblond et al., 2014). Thus, Shank3 haploinsufficiency is one of the most penetrant and prevalent monogenic causes of autism. Thus, there is an ongoing and unmet need for new approaches to therapy for PMS and ASD. The present disclosure is pertinent to these needs.

SUMMARY

The present disclosure involves methods for prophylaxis and/or therapy for PMS and/or ASD. The methods comprise administering to an individual in need thereof an effective amount of a histone methyltransferase (HMT) inhibitor, a histone deacetylase (HDAC) inhibitor, or a combination thereof, such that one or more symptoms of the PMS and/or the AMD are reduced. Without intending to be limiting, embodiments of the disclosure are illustrated using a representative HMT inhibitor (UNC0642) and a representative HDAC inhibitor (romidepsin). UNC0642, rescues autism-like social deficits in a Shank3-deficient model of autism. Further, romidepsin rescues autism-like social deficits in the Shank3-model, as well as in a BTBR T+tf/J mouse model. This latter model is known in the art to represent idiopathic autism and displays diverse autistic social deficits. But in contrast to these demonstrations, a variety of other drugs which may appear to be candidates for treating autism-like social deficits nevertheless fail to persistently rescue such deficits. In particular, fluoxetine, clozapine, aripiprazole, risperidone, valproic acid and Trichostatin A are all shown herein not to be able to reduce autism-like social deficits in Shank3-deficient mice. Thus, the disclosure provides unexpected benefits in approaching treatment of human disorders using the animal models used herein. In certain implementations performing a method of this disclosure improves one or more symptom of at least one autism-like social deficit. In embodiments, the improvement is observed after a single dose of the HMT or the HDAC inhibitor.

BRIEF DESCRIPTION OF THE FIGURES

FIG. 1. Treatment with the EHMT1/2 (euchromatic histone lysine methyltransferase 1 and 2) inhibitor, UNC0642, rescues autism-like social deficits in a Shank3-deficient mouse model. (a, b) Quantitative RT-PCR data on EHMT1 and EHMT2 mRNA levels and immunoblot data on the protein level of EHMT1, EHMT2 and histone methylation (H3K9me2, H3K4me3 and H3K27me3) in prefrontal cortex (PFC) from WT and Shank3$^{+/\Delta C}$ mice (a Shank3-deficient model of autism, which exhibit the loss of full-length Shank3 isoforms because of the deletion of C-terminal exon 21, Duffney et al., 2015). *P<0.05, **P<0.01, t-test. (c, d) Quantitative RT-PCR data on EHMT1 and EHMT2 mRNA levels and immunoblot data on the protein level of EHMT1, EHMT2 and H3K9me2 in postmortem tissue (Brodmann's Area 9) from human autism patients and healthy controls. *P<0.05, t-test. (e, f) Representative heat maps and bar graphs illustrating the time spent investigating either the social (Soc) or nonsocial (NS) stimulus from the social preference tests of juvenile male WT and Shank3$^{+/\Delta C}$ mice treated with saline (SAL) or UNC0642 (UNC, 1 mg/kg, i.p., once daily for 3 days). p<0.01, Soc vs. NS; ##p<0.01, p<0.05, saline vs. UNC, two-way ANOVA. (g) Dot plots illustrating the preference index (Sol vs. NS) in phase 2 of the 3-chamber social interaction assay in WT and Shank3$^{+/\Delta C}$ mice treated with saline or UNC. *: p<0.001, two-way ANOVA. (h) Plots of social preference index (mean±SEM) in saline-treated WT or UNC-treated Shank3$^{+/\Delta C}$ mice at pre- and multiple days post-treatments (two rounds). **: p<0.01, pre- vs. post-injection, two-way repeated measure ANOVA.

FIG. 2. Treatment with the HDAC (histone deacetylase) inhibitor Romidepsin rescues autism-like social deficits in multiple mouse models of autism. (a) Immunoblots and quantification analysis of the level of acetylated H3 in the nuclear fraction of cortical slices from WT or Shank3$^{+/\Delta C}$ mice injected with saline or romidepsin (RMD, 0.25 mg/kg, i.p., once daily for 3 days). *: p<0.05, two-way ANOVA. (b) Quantitative RT-PCR data on the mRNA level of class I HDAC family members (HDAC1, 2, 3, 8) in PFC from WT vs. Shank3$^{+/\Delta C}$ mice. P<0.01, t-test. (c) Quantitative RT-PCR showing HDAC2 mRNA in PFC from WT vs. Shank3$^{e4-9}$ mice (another Shank3-deficient model of autism, which exhibit the loss of major Shank3 isoforms because of the deletion of N-terminal exon 4-9, Wang et al., 2011). P<0.01, t-test. (d) Box plots showing the time spent investigating either the Soc or NS stimulus during 3-chamber sociability testing in juvenile male WT mice or Shank3$^{+/\Delta C}$ mice treated with romidepsin (0.25 mg/kg, i.p., 3×) or saline. P<0.01, saline vs. romidepsin; +++P<0.001, Soc vs. NS, two-way ANOVA. (e) Scatter plots showing the preference index of the sociability testing in individual WT or Shank3$^{+/\Delta C}$ mice treated with romidepsin or saline. *P<0.001, two-way ANOVA. (f) Representative heat maps from the social preference tests of WT and Shank3$^{+/\Delta C}$ mice treated with saline or RMD. (g) Plots of social preference index in Shank3$^{+/\Delta C}$ mice injected with romidepsin or saline at pre-dose and 1-21 days post-dose. : p<0.01, *: p<0.001, pre- vs. post-injection; ###: p<0.001, saline vs. romidepsin, two-way repeated measure (rm) ANOVA. (h) Scatter plots showing the social preference index of the 3-chamber sociability testing in individual Shank3e$^{4-9}$ mice before and after romidepsin treatment. **P<0.01, paired t-test. (i) Plots of social preference index in Shank3e$^{4-9}$ mice treated with romidepsin at different time points. *P<0.05, P<0.01, *P<0.001, pre- vs. post-injection, two-way rmANOVA. (j) Scatter Plots showing the social preference index in BTBR T+tf/J mice (a mouse model of idiopathic autism, which displays diverse autistic social deficits, McFarlane et al., 2008; Defensor et al., 2011) before and after romidepsin treatment. ***P<0.001, t-test.

FIG. 3. A variety of drugs fail to persistently rescue autism-like social deficits in Shank3-deficient mice. (a-f) Bar graphs (mean±SEM) showing the social preference index of the 3-chamber social interaction assay in Shank3$^{+/}$$_{\Delta C}$ mice treated with fluoxetine (10 mg/kg, i.p. once daily for 2 weeks, a), clozapine (5 mg/kg, i.p. once daily for 3 days, b), aripiprazole (1 mg/kg, i.p. once daily for 3 days, c), risperidone (0.1 mg/kg, i.p., once daily for 3 days, d), valproic acid (VPA, a mood stabilizer and a weak HDAC inhibitor, 100 mg/kg, i.p., once daily for 3 days, e) or Trichostatin A (TSA, a pan-HDAC inhibitor, 0.5 mg/kg, i.p., once daily for 3 days, f), at pre- and post-treatment time points. ###$P<0.001$, pre- vs. post-injection, one-way ANOVA.

DESCRIPTION OF THE DISCLOSURE

Unless defined otherwise herein, all technical and scientific terms used herein have the same meaning as commonly understood by one of ordinary skill in the art to which this disclosure pertains.

Unless specified to the contrary, it is intended that every maximum numerical limitation given throughout this description includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The present disclosure relates in part to results from large scale exome sequencing studies, which have identified many genes that are disrupted in autism as histone-modifying enzymes and chromatin remodelers (De Rubeis et al., 2014). Without intending to be bound by any particular theory, the present disclosure is based in part on an approach wherein epigenetic manipulation is used to restore gene expression, therefore inducing the long-lasting amelioration of social behavioral defects in PMS, and related disorders, including but not necessarily limited to ASD.

In one approach, the present disclosure involves use if inhibitors of histone methyltransferase (HMT), which can catalyze the mono-, di- or tri-methylation of lysine (K) residues on histone proteins to trigger gene activation or repression. In another approach, histone deacetylase (HDAC) family proteins are targeted using HDAC inhibitors. HDAC proteins generally exert their epigenetic silencing of gene expression via condensing the chromatin architecture. Prior to the present disclosure, the therapeutic potential of HMT- or HDAC-targeting agents for PMS and related disorders was largely unknown.

In various embodiments this disclosure comprises use of inhibitors of histone deacetylases and inhibitors of Histone-lysine N-methyltransferase known as EHMT1/2. The disclosure is illustrated using as a methyltransferase inhibitor the compound known in the as UNC0642, and the histone deactylase inhibitor known in the art as romidepsin.

UNC0642 is commercially available, and has the chemical name: 2-(4,4-Difluoro-1-piperidinyl)-6-methoxy-N-[1-(1-methylethyl)-4-piperidinyl]-7-[3-(1-pyrrolidinyl) propoxy]-4-quinazolinamin. In an embodiment it has the structure:

UNC0642

Romidepsin is sold under the trade name Istodax as an anticancer agent used in cutaneous T-cell lymphoma and other peripheral T-cell lymphomas. Romidepsin is a natural product produced by the bacterium *Chromobacterium violaceum*. It is sometimes referred to as depsipeptide. In an embodiment it has the structure it has the structure:

The disclosure includes pharmaceutically acceptable salts, partial salts, a hydrates, and stereoisomers of these compounds. It is also contemplated that other inhibitors can be used in methods of this disclosure, with the proviso that suitable compounds can cross the blood-brain barrier. Thus, compounds that cannot cross the blood brain barrier, or have been modified to preclude or limit blood-brain barrier crossing, are in certain embodiments not encompassed by the present disclosure. UNC0642 and romidepsin are referred to herein collectively as "inhibitors" as are their pharmaceutically acceptable salts, partial salts, a hydrates, and stereoisomers. Compounds that have chemical similarity and/or functional similarity to UNC0642, or to romidepsin, are included in this disclosure, provided they function therapeutically for ASD and/or PMS.

Other EHMT1/2 inhibitors that may function in treating the social deficits in PMS include:

UNC0638: an inhibitor of EHMT2 (IC50<15 nM) and EHMT1 (IC50=19 nM) with excellent potency and selectivity over a wide range of epigenetic and non-epigenetic targets.

A-366: a peptide-competitive inhibitor of EHMT2/EHMT1 with an enzymatic IC50 of ~3 nM and >100-fold selectivity over other methyltransferases and other non-epigenetic targets.

BIX01294: an inhibitor of EHMT2 with IC50 of 2.7 µM.

Other HDAC inhibitors that may function in treating the social deficits in PMS include:
Entinostat (MS-275; SNDX 275): strongly inhibits HDAC1 and HDAC3 with IC50 of 0.51 µM and 1.7 µM.

Vorinostat (Suberoylanilide hydroxamic acid, SAHA, Zolinza): the IC50 of vorinostat is 85 nM against HDAC1.

In certain embodiments, the individual treated according to this disclosure has not been diagnosed with cancer, and/or is not known to be at risk for developing cancer, including but not limited to blood cancers and lymphomas.

Compositions for performing any method of this disclosure may be prepared by mixing either or both types of inhibitors with any suitable pharmaceutically acceptable carriers, excipients and/or stabilizers. Some examples of compositions suitable for mixing with the compounds can be found in: Remington: The Science and Practice of Pharmacy (2005) 21st Edition, Philadelphia, Pa. Lippincott Williams & Wilkins.

In embodiments the disclosure includes administering a composition comprising a therapeutically effective amount of at least one inhibitor described herein. "Therapeutically effective amount" as used herein means that amount of the inhibitor that elicits the response that is being sought by a medical doctor or other clinician, and includes alleviation of one or more of the symptoms of the disease or disorder being treated, and/or reduction of the severity of one or more of the symptoms of the disease or disorder being treated. Thus, in certain embodiments, by administering a composition comprising an inhibitor to an individual in need thereof, the severity of at least one symptom in the individual is reduced, and/or there is a slowing of the progression of the symptom(s), or a cessation of the progression of the symptom(s), or elimination of the symptom. In certain embodiments, administration an inhibitor as described herein will result in a reduction in one or more symptoms by at least 10%, 20%, 30%, 50% or greater, up to a 75-90%, or 95% or greater, reduction in the one or more symptoms, compared to placebo-treated or other suitable control subjects, or any other suitable reference. In certain embodiments the reference can comprise a value, such as a value obtained from one or more control experiments, whether or not the experiments are performed concurrently with the administration of the inhibitors discussed herein. In certain approaches the control is a predicted value based on use of other compounds. In certain approaches, the disclosure provides for reducing any one or combination of autism or autism-like social deficits. In non-limiting embodiments, the disclosure provides for an improvement in one or more autism or autism-like social deficits that is greater than a control, wherein the control comprises an actual or predicted value for administration of a distinct compound, wherein the distinct compound can be any of various compounds known for use in treating psychiatric disorders, including but not necessarily limited to antipsychotic medications, such as aripiprazole, clozapine and risperidone, and antidepressants of the selective serotonin uptake inhibitor (SSRI) class, such as fluoxetine. In certain embodiments, the individual who is treated using approaches of this disclosure has one or more mutations in the Shank3 gene. Thus, a candidate for treatment using a method of this disclosure may be identified by determining mutations in the individual's Shank3 gene, and if such mutation(s) are present, a composition as described herein is administered to the individual. Shank3 mutations associated with, for example, PMS are known in the art. Further, mouse models where Shank3 is disrupted are known in the art as being clinically pertinent to ASD and PMS. (See, for example, Yoo J, Bakes J, Bradley C, Collingridge G L, Kaang B-K. Shank mutant mice as an animal model of autism. *Philosophical Transactions of the Royal Society B: Biological Sciences*. 2014; 369(1633):20130143; doi: 10.1098/rstb.2013.0143, the disclosure of which is incorporated herein by reference). Likewise, certain demonstrations of this disclosure are provided and use the BTBR T+tf/J mouse model, which is also known in the art to be clinically pertinent to autism. (See, for example, McFarlane H G, Kusek G K, Yang M, Phoenix J L, Bolivar V J, Crawley J N (2008) Autism-like behavioral phenotypes in BTBR T+tf/J mice. *Genes Brain Behav.* 2008 March; 7(2):152-63; doi: 10.1111/j.1601-183X.2007.00330.x, the disclosure of which is incorporated herein by reference).

The compositions of the invention can be administered using any suitable method and route of administration. Some non-limiting examples include oral, parenteral, subcutaneous, intraperitoneal, intrapulmonary, intranasal, intracranial, and can be performed using an implantable device, such as an osmotic pump. Parenteral infusions include intramuscular, intravenous, intraarterial, intraperitoneal, pulmonary instillation as mist or nebulization, and subcutaneous administration.

In certain embodiments, the disclosure includes an article of manufacture comprising one or more of the inhibitors, suitable containers, and packaging, wherein the packaging contains printed material which provides an indication that the contents of the package are to be used prophylaxis and/or therapy of ASD and/or PMS. The packaging can include one or more sealed containers comprising the inhibitor(s).

Administration of the inhibitor can be performed in conjunction with conventional therapies that are intended to treat the ASD and/or PMS. For example, a composition comprising the inhibitor could be administered prior to, concurrently, or subsequent to conventional therapies known to those skilled in the art for prophylaxis or therapy of, for example, ASD or PMS or other disorders that manifest in pronounced social defects. Such therapies include but are not limited to combining treatment with an inhibitor as described herein with other pharmaceutical agent(s) known to be effective against the particular condition being treated, behavioral and physical therapies, cognitive therapies, and the like.

Routes and frequency of administration of the inhibitors, as well as dosage, will vary from individual to individual, and may be readily established using standard techniques given the benefit of the present disclosure. As discussed above, and without intending to be constrained by any particular theory, it is considered that the results presented herein indicate that approaches of this disclosure will be suitable for providing treatment for ASD and PMS. In embodiments, one or more doses are administered. In embodiments, an individual treated according to this disclosure has been diagnosed with or is suspected of having ASD or PMS or related conditions, which can include but are not necessarily limited to Asperger's syndrome, Rett's syndrome, pervasive developmental disorder not otherwise specified (PDD-NOS), childhood disintegrative disorder, semantic communication disorder, non-verbal learning disabilities, hyperlexia, and attention deficit hyperactivity disorder. In embodiments, the individual is male or female.

In embodiments the disclosure relates to treating patients who are diagnosed with or are suspected of having ASD and/or PMS, and is expected to be pertinent to any subject, such as an adult human, child or infant, who has ASD or PMS. In certain aspects, the disclosure comprises treating patients who have been identified as or are suspected of having a monogenic cause of ASD-like social deficits, such as patients who have PMS. In this regard, and as is known in the art, ASD comprises a group of disorders generally characterized by varying degrees of impairment in communication skills, social interactions, learning disabilities, and restricted and/or repetitive behaviors which range from mild to severe degrees of impairment. Symptoms of ASD (and accordingly PMS) include but are not necessarily limited to social withdrawal, reluctance to make eye contact/averted gaze, obsessions and repetitive behavior, attention deficit, anxiety, hyperactivity, depression, and the inability to comprehend feelings of others. Some ASD patients ignore communication from others, and/or have an aversion to physical contact and/affection. Communication difficulties range from a complete lack of verbal communication, to monotone speech and/or inappropriate volume. ASD patients may also experience visual difficulties, sound and light sensitivity, and mental retardation. It is expected that any one or any combination of these symptoms can be improved using embodiments of this disclosure.

In an embodiment of the disclosure, administration of an effective amount of an inhibitor to a subject presenting with ASD and/or PMS symptoms will detectably decrease, eliminate, or prevent the symptom(s). In an embodiment, administration of an effective amount the inhibitor will result in an improvement of an assessment in an autism diagnostic measurement, such as Autism Diagnostic Observation Schedule (ADOS), and/or the Autism Diagnostic Interview-Revised (ADI-R). In embodiments, administration of an effective amount of an inhibitor to a subject presenting with ASD and/or PMS symptoms will improve one or more scores relative to the specified diagnostic cut-off threshold in at least one of the five domains of the ADOS. In this regard, the scores measure impairment, thus the higher the number, the more severe the impairment. In embodiments, a reduction in impairment can be evidenced by an improvement in ADOS scores for: communication; reciprocal social interaction; communication and social; and combinations thereof. In embodiments, administration of an inhibitor according to this disclosure results in a change in an ASD assessment score such that the score changes favorably relative to a threshold value. In embodiments, treating patient according to this disclosure results in a reduction in repetitive behavior, and/or an improvement on a cognitive learning test, and/or an improvement in or more oral communication skills and/or improvements in social interaction behavior. In embodiments, the treatment results in an increased preference for a social stimulus relative to a non-social stimulus. In embodiments, the improvement in one or any combination of symptoms described herein is durable and can last for example, for 1, 2, 3, 4, 5, 6, 7, 8, 9, 10, 11, 12, 13, 14, 15, 16, 17, 18, 19, 20, 21, days, or more, such as up to one month, two months, three months, four months, five months, six months, of more, subsequent to a single administration or a single dosing period. In certain embodiments, a single dosing period comprises an administration of once daily, at least once daily, or not more than once daily, for a period of days, such as for 2 days, 3 days, 4, days, 5 days, days, 6, days, or 7 days. The disclosure also provides for repeated administrations, i.e., repeated dosing periods.

The following example is meant to illustrate but not limit the disclosure.

Example 1

Figure 1:
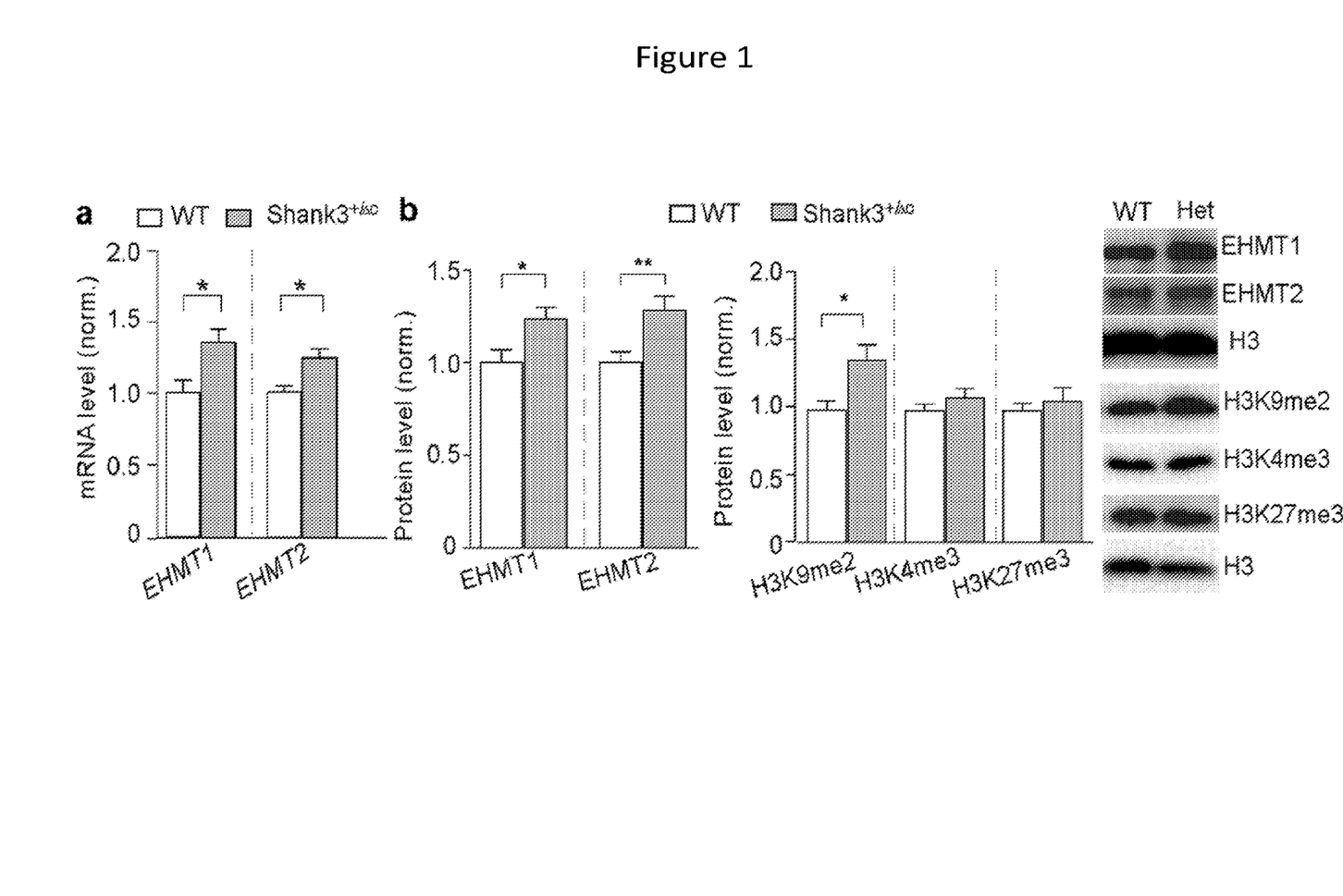

We analyzed the global histone methylation linking to transcriptional repression (H3K9Me2, H3K27Me3) or activation (H3K4Me3) in frontal cortex of Shank3+/ΔC mice. As shown in FIG. 1A, the level of H3K9Me2 in Shank3+/ΔC mice was significantly higher than wild-type mice (n=5 pairs, p<0.05, t-test), suggesting that Shank3-deficient mice have an abnormally high level of histone dimethylation at lysine 9. We then analyzed whether the autism-like social deficits in Shank3-deficient mice could be rescued by specific inhibition of EHMT1 and EHMT2, the two euchromatic histone methyltransferases specifically catalyze H3K9 dimethylation. UNC0642, discussed above, is a highly potent and selective inhibitor of EHMT1 and EHMT2, which exhibits >2,000-fold to >20,000-fold selectivity for EHMT1/2 over other methyltransferases and displays modest brain penetration in vivo (Liu et al., 2013).

To test the social preference behavior, juvenile male Shank3+/ΔC mice and age-matched wild-type (WT) mice were subject to the three-chamber social interaction assay, as previously described (Duffney et al., 2015). Briefly, the test is composed of three phases with various stimuli placed in each of two side chambers. Phase 1 contains two identical nonsocial stimuli (NS1 & NS1), phase 2 contains a nonsocial stimulus (NS1) and a social stimulus (Soc1), and phase 3 contains a known social stimulus (Soc1) and a novel social stimulus (Soc2). The preference index for one stimulus over the other stimulus in each phase was compared.

We previously found that when presented with two identical non-social stimuli (NS1-NS1, phase 1), no preference was observed in either genotype (Duffney et al., 2015). During the presentation of both a social and a non-social stimuli (Soc1-NS1, phase 2), WT mice spent significantly more time exploring the social stimulus over the non-social object, while Shank3$^{+/\Delta C}$ mice showed a significant loss of the preference for the social stimulus (WT: 126.1±6.8 sec, n=52; Shank3$^{+/\Delta C}$: 60.6±3.0 sec, n=52, p<0.001, ANOVA). The significantly reduced social preference index in Shank3-deficient mice (WT: 64.3%±1.9%, n=53; Shank3$^{+/\Delta C}$: 20.7%±2.5%, n=57, p<0.001, t-test) suggests an impairment of sociability. When exposed to two social stimuli (Soc2-Soc1, phase 3), both genotypes displayed similar preference for the novel over the familiar social stimulus, suggesting that Shank3-deficient mice have intact social novelty recognition memory. In the sociability assay, we found that a brief treatment with the EHMT1/2 inhibitor UNC0642 (1 mg/kg, i.p., once daily for 3 days) significantly elevated the preference for the social stimulus (Soc) over the non-social object (NS) in Shank3$^{+/\Delta C}$ mice (FIG. 1B-D, WT+SAL: 62.0%±3.1%, n=14, Shank3$^{+/\Delta C}$+SAL: 22.5%±3.3%, n=14, Shank3$^{+/\Delta C}$+UNC: 48.9%±2.3%, n=12, WT+UNC: 53.4%±5.1%, n=11, p<0.01, ANOVA). This therapeutic effect of UNC0642 lasted for ~15 days post-injection, and was still effective with the repeated administration (FIG. 1E, n=4 each group, p<0.01, ANOVA), suggesting that UNC0642 can lead to prolonged rescue of social deficits in the Shank3 model of PMS. A battery of other behavioral assays did not reveal abnormalities in UNC0642-treated mice (data not shown), which is considered to have ruled out the existence of severe side effects.

Figure 2:
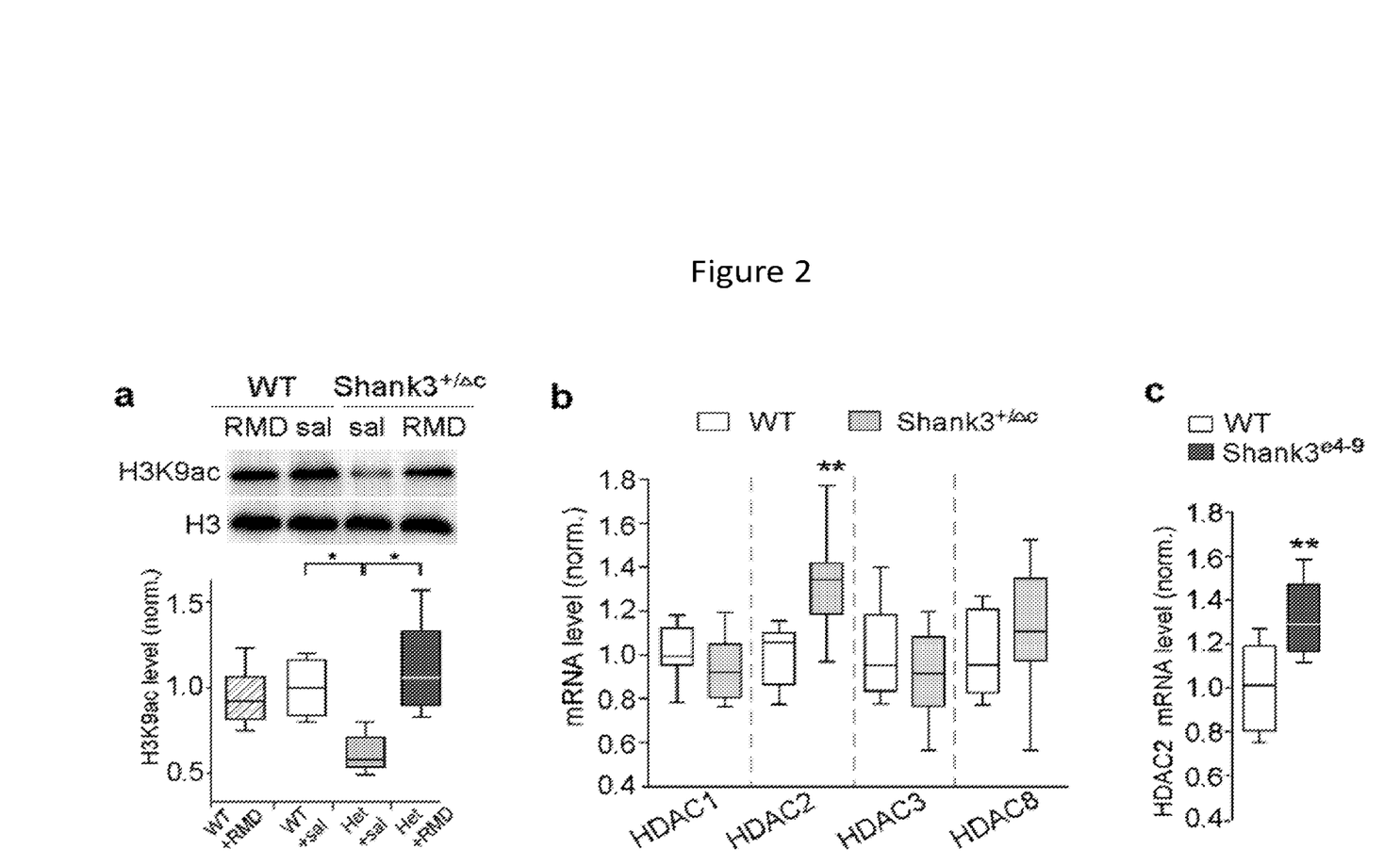

To analyze the potential role of HDACs in PMS, we examined the level of global histone acetylation in the frontal cortex of Shank3$^{+/\Delta C}$ mice. As shown in FIG. 2A, the level of acetylated H3 in cortical slices from Shank3$^{+/\Delta C}$ mice (saline-injected) was significantly lower than that from wild-type mice. A systemic administration of the low dose romidepsin (0.25 mg/kg, i.p., once daily for 3 days), a highly potent (nanomolar potency) and brain-permeable class I-specific HDAC inhibitor (Klimek et al., 2008), significantly elevated the level of acetylated H3 in Shank3$^{+/\Delta C}$ mice (n=6 each group, p<0.05, two-way ANOVA). It suggests that Shank3-deficient mice have an abnormally low level of histone acetylation, which can be restored by romidepsin treatment.

To examine the impact of romidepsin on autism-like social deficits in Shank3-deficient mice, we performed the 3-chamber social interaction assay. Remarkably, we found that romidepsin treatment (0.25 mg/kg, i.p., 3×) significantly elevated the preference for the social stimulus (Soc) over the non-social object (NS) in Shank3$^{+/\Delta C}$ mice (FIG. 2B), and this effect of romidepsin lasted for 21 days post-injection (FIG. 2C, n=12, p<0.01, two-way rmANOVA). No social improvement was found in saline-injected Shank3$^{+/\Delta C}$ mice (n=7). These results suggest that romidepsin can lead to the prolonged rescue of social deficits in the Shank3 model of PMS.

Romidepsin has been approved by the FDA for treatment of cutaneous T-cell lymphoma. The identified dose of romidepsin effective in PMS treatment (0.25 mg/kg) is much lower than that used for cancer treatment (~5% of human anti-cancer dose). This low dose romidepsin treatment does not induce behavioral impairment or neuronal loss in juvenile animals (data not shown), suggesting that this repurposed therapeutics is safe to be used in young subjects. It has been estimated that 1-month interval in juvenile mice (from 1-mo to 2-mo) may be equivalent to 6-year period in young humans (from 14-yr to 20-yr). Thus, the long-lasting therapeutic effect of a single treatment with romidepsin is very promising for treatment of human patients with PMS or related disorders, such as ASD.

Figure 3:
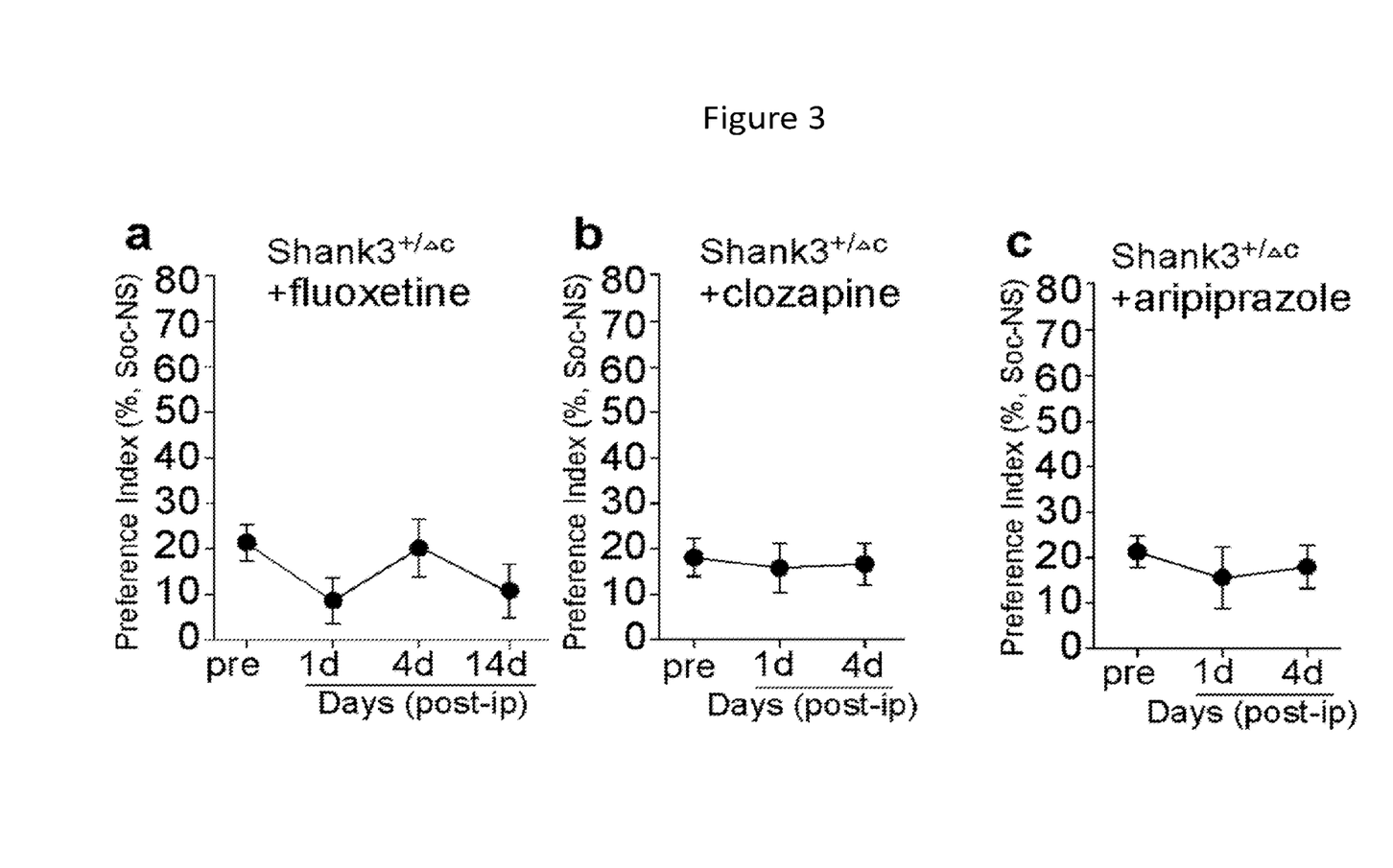

We further examined whether the pharmacological agents currently used for various psychiatric disorders are able to rescue social deficits in Shank3$^{+/\Delta C}$ mice. The SSRI antidepressant fluoxetine (10 mg/kg, i.p. once daily for 2 weeks) failed to induce any improvement of the social preference in the three-chamber social interaction assay (FIG. 3A, n=8, p>0.05, ANOVA). The atypical antipsychotics clozapine (5 mg/kg, i.p. once daily for 3 days) was also ineffective in rescuing the social deficits in Shank3+/° c. mice (FIG. 3B, n=6, p>0.05, ANOVA). No improvement on social preference was observed with aripiprazole (1 mg/kg, i.p. once daily for 3 days, FIG. 3C, n=6, p>0.05) or risperidone (0.1 mg/kg, i.p. once daily for 3 days, FIG. 3D, n=6, p>0.05), the only drugs approved by FDA for autism treatment. These data are consistent with the lack of effect of these drugs on the social communication deficit observed in ASD despite their utility in managing irritability and repetitive behaviors (McPheeters et al., 2011). These data suggest that the potent and prolonged therapeutic effectiveness of UNC0642 or romidepsin on autism-like social deficits is very unique.

We assessed the safety and potential side effects associated with UNC0642 (1 mg/kg, i.p., once daily for 3 days) or romidepsin (0.25 mg/kg, i.e. 0.75 mg/m$^2$, i.p., once daily for 3 days) treatment by performing a general health screening and other behavioral assays in Shank3$^{+/\Delta C}$ mice. In blood chemistry and hematological analyses, all the indicators for liver and kidney functions, as well as lipid and protein metabolism, were within normal ranges. The lower white blood cells and lymphocytes were observed in romidepsin-treated mice. As FDA safety studies indicated, this side effect is transient and disappears after the termination of drug administration. No behavioral abnormalities or neuronal loss were found in UNC0642- or romidepsin-treated mice. It suggests the general safety of both compounds, consistent with the lack of toxicity of UNC0642 treatment at a higher dose and longer duration (5 mg/kg, i.p. 5 days, Kim et al., 2017), and the safety profile of romidepsin as an FDA-approved anti-cancer drug in humans (14 mg/m², i.v., once a week for 3 weeks).

REFERENCES

Betancur C, Buxbaum J D (2013) SHANK3 haploinsufficiency: a "common" but underdiagnosed highly penetrant monogenic cause of autism spectrum disorders. Mol Autism. 4:17.

Bonaglia, M. C., R. Giorda, R. Borgatti, G. Felisari, C. Gagliardi, A. Selicorni and O. Zuffardi (2001). Disruption of the ProSAP2 gene in a t(12;22)(q24.1;q13.3) is associated with the 22q13.3 deletion syndrome. Am J Hum Genet 69: 261-268.

De Rubeis S, He X, Goldberg A P, Poultney C S, Samocha K, et al. (2014) Synaptic, transcriptional and chromatin genes disrupted in autism. Nature. 515:209-15.

Duffney L J, Zhong P, Matas E, Wei J, Cheng J, Dietz D M, Kajiwara Y, Buxbaum J D, Yan Z (2015) Autism-like deficits in Shank3-deficient mice are rescued by targeting actin regulators. Cell Reports 11:1400-1413.

Durand, C. M., C. Betancur, T. M. Boeckers, J. Bockmann, P. Chaste, et al. (2007). Mutations in the gene encoding the synaptic scaffolding protein SHANK3 are associated with autism spectrum disorders. Nat Genet 39: 25-27.

Klimek V M, Fircanis S, Maslak P, Guernah I, Baum M, Wu N, Panageas K, Wright J J, Pandolfi P P, Nimer S D (2008) Tolerability, pharmacodynamics, and pharmacokinetics studies of depsipeptide (romidepsin) in patients with acute myelogenous leukemia or advanced myelodysplastic syndromes. Clin Cancer Res. 14:826-32.

Leblond C S, Nava C, Polge A, Gauthier J, Huguet G, Lumbroso S, et al., (2014). Meta-analysis of SHANK Mutations in Autism Spectrum Disorders: a gradient of severity in cognitive impairments. PLoS Genet. 10:e1004580.

McPheeters M L, Warren Z, Sathe N, Bruzek J L, Krishnaswami S, Jerome R N, Veenstra-Vanderweele J. (2011) A systematic review of medical treatments for children with autism spectrum disorders. Pediatrics 127, e1312e1321.

Moessner, R. Marshall C R, Sutcliffe J S, Skaug J, Pinto D, Vincent J, Zwaigenbaum L, Fernandez B, Roberts W, Szatmari P, Scherer S W (2007). Contribution of SHANK3 mutations to autism spectrum disorder. Am. J. Hum. Genet. 81: 1289-1297.

Wang X, McCoy P A, Rodriguiz R M, Pan Y, Je S, et al. (2011) Synaptic dysfunction and abnormal behaviors in mice lacking major isoforms of Shank3. Hum Mol Genet 20:3093-3108.

McFarlane H G, Kusek G K, Yang M, Phoenix J L, Bolivar V J, Crawley J N (2008) Autism-like behavioral phenotypes in BTBR T+tf/J mice. Genes Brain Behav., 7:152-163.

Defensor E B, Pearson B L, Pobbe R L, Bolivar V J, Blanchard D C, Blanchard R J (2011) A novel social proximity test suggests patterns of social avoidance and gaze aversion-like behavior in BTBR T+tf/J mice. Behav. Brain Res., 217: 302-308.

Kim, Y., Lee, H. M., Xiong, Y., Sciaky, N., Hulbert, S. W., Cao, X., Everitt, J. I., Jin, J., Roth, B. L., and Jiang, Y. H. (2017). Targeting the histone methyltransferase G9a activates imprinted genes and improves survival of a mouse model of Prader-Willi syndrome. Nature medicine 23, 213-222.

Center for Drug Evaluation and Research, Application Number: 22-393, Pharmacology Review(s) www.accessdata.fda.gov/drugsatfda_docs/nda/2009/022393s000_PharmR_P1.pdf While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

What is claimed is:

1. A method for therapy for Phelan-McDermid Syndrome (PMS) and/or autism spectrum disorder (ASD) in an individual comprising administering to the individual a therapeutically effective amount of a histone methyltransferase (HMT) inhibitor, a histone deacetylase (HDAC) inhibitor, or a combination thereof, wherein:

if the individual has been diagnosed with the PMS, the HMT inhibitor administered is UNC0642, the HDAC inhibitor administered is romidepsin, or a combination of UNC0642 and romidepsin is administered; and if the individual has been diagnosed with the ASD, the HMT inhibitor administered is UNC0642, or a combination of the UNC0642 and the romidepsin is administered.

2. The method of claim 1, wherein the individual has been diagnosed with the PMS and/or the ASD, and the HMT inhibitor administered is UNC0642.

3. The method of claim 1, wherein the individual has been diagnosed with the PMS and the HDAC inhibitor administered is romidepsin.

4. The method of claim 1, wherein the individual has not been diagnosed with cancer.

5. The method of claim 1, wherein the individual has not been diagnosed with cancer.

6. The method of claim 1, wherein subsequent to the administration an improvement in a symptom comprising at least one autism-like social deficit occurs.

7. The method of claim 6, wherein the improvement occurs after a single dosing period of administration of the inhibitor.

8. The method of claim 1, wherein the individual has a mutation in a Shank3 gene.

9. The method of claim 1, wherein the individual has been diagnosed with the PMS and the combination of the UNC0642 and the romidepsin is administered.

10. The method of claim 1, wherein individual has been diagnosed with the ASD and the combination of the UNC0642 and the romidepsin is administered.

* * * * *